United States Patent [19]

Cohen

[11] Patent Number: 5,054,485

[45] Date of Patent: Oct. 8, 1991

[54] HEMODYNAMICALLY RESPONSIVE SYSTEM FOR AND METHOD OF TREATING A MALFUNCTIONING HEART

[75] Inventor: Todd J. Cohen, San Francisco, Calif.

[73] Assignee: Leonard Bloom, Towson, Md.; a part interest

[21] Appl. No.: 531,867

[22] Filed: Jun. 1, 1990

[51] Int. Cl.$^5$ .................................................. A61N 1/00
[52] U.S. Cl. ........................ 128/419 D; 128/419 PG
[58] Field of Search ................... 128/419 PG, 419 D

[56] References Cited

U.S. PATENT DOCUMENTS

| | | | |
|---|---|---|---|
| 3,614,954 | 10/1971 | Mirowski et al. | 128/419 D |
| 3,942,536 | 3/1976 | Mirowski et al. | 128/419 D |
| 4,164,946 | 8/1979 | Langer | 128/419 D |
| 4,184,493 | 1/1980 | Langer et al. | 128/419 D |
| 4,202,340 | 5/1980 | Langer et al. | 128/419 D |
| 4,210,149 | 7/1980 | Heilman et al. | 128/419 D |
| 4,223,678 | 9/1980 | Langer et al. | 128/419 D |
| 4,254,775 | 3/1981 | Langer | 178/419 D |
| 4,291,699 | 9/1981 | Geddes et al. | 178/419 D |
| 4,295,474 | 10/1981 | Fischell | 128/697 |
| 4,300,567 | 11/1981 | Kolenik et al. | 128/419 D |
| 4,303,075 | 12/1981 | Heilman et al. | 128/419 PG |
| 4,316,472 | 2/1982 | Mirowski et al. | 128/419 D |
| 4,323,075 | 4/1982 | Langer | 128/419 D |
| 4,393,877 | 7/1983 | Imran et al. | 128/705 |
| 4,403,614 | 9/1983 | Engle et al. | 128/419 D |
| 4,407,288 | 10/1983 | Langer et al. | 128/419 PG |
| 4,427,011 | 1/1984 | Spurrell et al. | 128/419 D |
| 4,440,172 | 4/1984 | Langer | 128/419 D |
| 4,475,551 | 10/1984 | Langer et al. | 128/419 D |
| 4,523,595 | 6/1985 | Zibell | 128/419 D |
| 4,548,203 | 10/1985 | Tacker, Jr. et al. | 128/419 D |
| 4,548,209 | 10/1985 | Wielders et al. | 128/419 D |
| 4,559,946 | 12/1985 | Mower | 128/419 D |
| 4,562,846 | 1/1989 | Cox et al. | 128/69 G |
| 4,572,191 | 2/1980 | Mirowski et al. | 128/419 D |
| 4,576,170 | 3/1980 | Bradley et al. | 128/419 D |
| 4,592,367 | 6/1980 | Imran | 128/706 |
| 4,614,192 | 9/1986 | Imran et al. | 128/419 D |
| 4,625,730 | 12/1980 | Fountain et al. | 128/419 D |
| 4,662,377 | 5/1987 | Heilman et al. | 128/419 D |
| 4,693,253 | 9/1987 | Adams | 128/419 D |
| 4,708,143 | 11/1987 | Schroeppel | 128/419 PG |
| 4,730,619 | 3/1988 | Koning et al. | 128/419 PG |
| 4,733,667 | 3/1988 | Olive et al. | 128/419 D |
| 4,770,177 | 9/1988 | Schroeppel | 128/419 PG |
| 4,774,950 | 10/1988 | Cohen | 128/419 D |
| 4,799,493 | 1/1989 | DuFault | 128/705 |
| 4,802,481 | 2/1989 | Schroeppel | 128/419 PG |
| 4,803,987 | 2/1989 | Calfee et al. | 128/419 PG |
| 4,819,662 | 4/1989 | Heil, Jr. et al. | 128/419 P |
| 4,867,160 | 9/1989 | Schaldack | 128/419 PG |
| 4,873,980 | 10/1989 | Schaldack | 128/419 PG |
| 4,895,151 | 1/1990 | Grevis et al. | 128/419 G |
| 4,967,748 | 11/1990 | Cohen | 128/419 D |

OTHER PUBLICATIONS

Mirowski et al., "Standby Automatic Defibrillator, An Approach to Prevention of Sudden Coronary Death", Arch. Intern. Med., vol. 126, pp. 158-161, (Jul. 1970).

(List continued on next page.)

Primary Examiner—Francis Jaworski
Assistant Examiner—George Manuel
Attorney, Agent, or Firm—Leonard Bloom

[57] ABSTRACT

A system for and method of treating a malfunctioning heart is based on hemodynamics, the pressure in the right side of a patient's circulatory system being sensed. A first signal is developed representative of mean right atrial pressure (MRAP) and a second signal is developed representing right ventricular systolic pressure (RVSP). When the difference (or ratio) between MRAP and RVSP reaches at least a predetermined value, the combination being an indication of hemodynamic compromise, cardioversion/defibrillation is effected. In these cases, a heart rate criterion, for example a rate over 150 bpm, may also have to be met before cardioverting/defibrillation is initiated. Fixed or variable baselines against which the predetermined value is to be measured may be provided. Other hemodynamic parameters, such as RVDP, RVSP, MRVP and/or MAP could be used as one or another of the hemodynamic parameters.

43 Claims, 6 Drawing Sheets

OTHER PUBLICATIONS

Mirowski et al., "Transvenous Automatic Defibrillator–Preliminary Clinical Tests of its Defibrillating Subsystem", Trans. Amer. Soc. Artif. Int. Organs, vol. XVIII, pp. 520–524, (1972).

Morowski et al., "The Development of the Transvenous Automatic Defibrillator", Arch. Intern. Med., vol. 128, pp. 773–779, (May 1972).

Mirowski et al., "The Automatic Implantable Defibrillator", Department of Medicine, Sinai Hospital of Baltimore, Maryland U.S.A. (Aug. 3, 1981).

Cohen, "A Theoretical Right Atrial Pressure Feedback Heart Rate Control System to Restore Physiological Control to the Rate-Limited Heart", PACE, vol. 7, (Jul.–Aug., 1984).

Luceri et al., "Implantable Devices for the Treatment of Cardiac Arrhythmias", Cardiology Clinics, vol. 3, No. 1 (Feb., 1985).

Mirowski, "The Automatic Implantable Cardioverter–Defibrillator: An Overview", JACC, vol. 6, No. 2, pp. 461–466 (Aug., 1985).

Mirowski et al., "Recent Clinical Experience with the Automatic Implantable Cardioverter–Defibrillator", Medical Instrumentation, vol. 20, pp. 285–291, (1986).

Olson et al., "Automatic Detection of Ventricular Fibrillation with Chronically Implanted Pressure Sensors", (Abstract), JACC, vol. 7, No. 2, p. 182A, (Feb. 1986).

Sharma et al., "Right Ventricular Pressure During Ventricular Fibrillation in Man: Potential Implications for Implantable Antitachycardia Devices", (Abstract No. 0878), Supplemental II Circulation, vol. 78, No. 4, p. II-220, (Oct. 1988).

HEMODYNAMICALLY RESPONSIVE SYSTEM FOR AND METHOD OF TREATING A MALFUNCTIONING HEART

CROSS REFERENCE TO RELATED APPLICATION

The present application relates to material which can be viewed as an improvement over the subject matter claimed in applicant's copending application Ser. No. 385,544, now U.S. Pat. No. 4,984,572 filed on July 27, 1989 and entitled "HEMODYNAMICALLY RESPONSIVE SYSTEM FOR AND METHOD OF TREATING A MALFUNCTIONING HEART", the disclosure of which is incorporated herein in its entirety by reference.

BACKGROUND OF THE INVENTION

1. Field of the Invention

This invention relates to a system for and method of treating a malfunctioning heart and, more particularly, to such a system and method which effects cardioversion/defibrillation in response to sensing a heart malfunction. The invention is concerned with a system and method which involves sensing hemodynamic pressure parameters at at least two sites, for example the right atrium and the right ventricle, and effecting cardioversion/defibrillation when hemodynamic compromise is indicated. The invention also involves a system and method in which two hemodynamic pressure parameters at a single site, for example the right ventricle, and effecting cardioversion/defibrillation when hemodynamic compromise is indicated. The invention provides for the cardioverting/defibrillation of a malfunctioning heart as well as the possibility of overcoming a tachycardia manifestation without resorting to either cardioverting or defibrillating.

2. Description of the Prior Art

In recent years, substantial progress has been made in pacemakers and in the development of cardioverting-/defibrillating techniques for effectively treating various heart disorders and arrhythmias. Past efforts have resulted in the development of implantable electronic pacemakers and standby cardioverters-defibrillators which, in response to the detection of an abnormal cardiac rhythm, discharge sufficient energy via electrodes connected to the heart to depolarize and restore it to normal cardiac rhythm. An early example of this cardioverting/defibrillating technique is disclosed in U.S. Pat. No. 3,942,536 of Mirowski et al., the technique involving responses to a sensed peak right ventricular threshold pressure dropping to a fixed predetermined level. This known technique did not involve sensing pressure at more than one site nor the determination of more than one pressure parameter, for example mean pressure at a single site and systolic pressure at the site.

Efforts have also been directed toward developing techniques for reliably monitoring heart activity in order to determine whether cardioversion/defibrillation are desirable or necessary. Such techniques include monitoring ventricular rate or determining the presence of fibrillation on the basis of a probability density function (PDF). A system using the PDF technique statistically compares the location of points of a cardiac waveform with the expected locations of points of the normal waveform. When the waveform becomes irregular, as measured by its probability density function, an abnormal cardiac function is suggested. The latter technique is described in U.S. Pat. Nos. 4,184,493 and 4,202,340 both of Langer et al.

A more recent system, as disclosed in U.S. Pat. No. 4,475,551 of Langer et al. utilizes both the PDF technique to determine the presence of an abnormal cardiac rhythm and a heart rate sensing circuit for distinguishing between ventricular fibrillation and high rate tachycardia (the latter being indicated by a heart rate above a predetermined minimum threshold), on the one hand, and normal sinus rhythm or a low rate tachycardia (indicated by a heart rate falling below a pre-determined minimum threshold), on the other hand.

Still further, research in this area has resulted in the development of a heart rate detector system which accurately measures heart rate from a variety of different electrocardiogram (ECG) signal shapes. One such system is disclosed in U.S. Pat. No. 4,393,877 of Imran et al.

Despite these past efforts and the level of achievement prevalent among prior art systems, there are potential difficulties and drawbacks which may be experienced with such devices.

A system for and method of treating a malfunctioning heart based on hemodynamics at a single site in a circulatory system has been disclosed in U.S. Pat. No. 4,774,950 of Todd J. Cohen, granted Oct. 4, 1988. The dynamics of mean arterial pressure (MAP) mean right atrial pressure (MRAP), mean right ventrical pressure (MRVP), mean left atrial pressure (MLAP), mean left ventrical pressure (MLVP) or mean central venous pressure (MCVP) were respectively proposed as the single-site or single-parameter basis for cardioversion/defibrillation.

Most current antitachycardia systems detect arrhythmias primarily by sensing rate and perform inadequately in the differentiation of hemodynamically stable from unstable rhythms. These devices, for example, may fire during a stable supraventricular tachycardia (SVT) inflicting pain and wasting energy; damage to the heart may result.

A commonly used implantable antitachycardia device is the automatic implantable cardioverter-defibrillators (AICD) which is commercially available under the model designations 1500, 1510 and 1520 from Cardiac Pacemakers, Inc. whose address is: 4100 North Hamlin Avenue, St. Paul, MN 55164. These devices continuously monitor myocardial electrical activity, detecting ventricular tachycardia (VT) and ventricular fibrillation (VF), and delivering a shock to the myocardium to terminate the arrhythmia. The AICD has been shown to reduce the mortality rate in patients with malignant arrhythmias with initial studies at Johns Hopkins Hospital and Stanford Medical Center demonstrating a 50 percent decrease in the anticipated total incidence of death, as reported by Mirowski et al., "Recent Clinical Experience with the Automatic Implantable Cardioverter-Defibrillator", *Medical Instrumentation*, Vol. 20, pages 285-291 (1986). Arrhythmias are detected by (1) a rate (R wave) sensor and (2) a probability density function (PDF) which defines the fraction of time spent by the differentiated electrocardiogram between two amplitude limits located near zero potential. Presently, the functional window of the PDF is wide to permit the detection of both VT and VF, and therefore, this device functions essentially as a rate-only sensing system. As reported by Mirowski, "The Automatic Implantable Cardioverter-Defibrillator: An Overview", JACC, Vol. 6, No. 2, pages 461–466, (August, 1985), when an arrhythmia fulfills either the rate or PDF criteria, the device delivers Schuder's truncated exponential pulse of 25 Joules some 17 seconds after the onset of the arrhythmia. The device can recycle as many as three times if the previous discharge is ineffective with the strength of the second, third and fourth pulses being increased to 30 Joules. After the fourth discharge, approximately 35 seconds of nonfibrillating rhythm are required to reset the device. The Mirowski et al., supra, and the Mirowski, supra publications set out, in summary form, background material relating to the defibrillating/cardioverting arts against which the present invention was made.

In addition to the standard automatic implantable cardioverter-defibrillator characterized by the above-noted, dual detection algorithm, a variant of the device which features a sensing system that relies only on the analysis of heart rate is also available. This "rate-only" version of the known cardioverter-defibrillator preferred by some investigators, is more sensitive than the dual detection version unit and theoretically less likely to miss ventricular tachycardias with narrow QRS complexes. It is believed that the "rate-only" system, on the other hand, may be too sensitive, delivering cardioverting/defibrillating pulses too often or too soon, no hemodynamic parameter having been taken into consideration.

One problem with current systems is that they function primarily as a rate-only sensing systems and may fire for nonmalignant as well as malignant tachycardias. These firings are not benign; potentially endangering myocardium, wasting energy and inflicting pain on the conscious patient, all distinct shortcomings and disadvantages.

SUMMARY OF THE INVENTION

The principal object of the present invention is to provide a system for cardioverting/defibrillating which avoids unnecessary firings, thereby reducing the danger to the myocardium, saving energy and avoiding pain.

Another object of the present invention is to provide an implantable system for cardioverting/defibrillating which avoids unnecessary firings, thereby reducing the danger to the myocardium, saving energy and avoiding pain.

A further object of the present invention is to provide a system for cardioverting/defibrillating which is hemodynamically responsive to relationships between hemodynamic parameters, such as pressure, at at least two sites or to more than one hemodynamic parameter at one site in the circulatory system of a patient.

An additional object of the present invention is to provide a system for cardioverting/defibrillating which is hemodynamically responsive to relationships between selected parameters (difference or ratio) from a baseline (either fixed or varying).

Yet another object of the present invention is to provide a system for cardioverting/defibrillating having the above-noted characteristics which is also, responsive to heart beating rate criterion.

Yet another object of the present invention is to provide a method of cardioverting/defibrillating which may be advantageously carried out using a cardioverter-defibrillator constructed in accordance with the present invention.

From one viewpoint, the invention can be seen as being in a system for treating a malfunctioning heart of the type which includes storage means for storing electrical energy and electrode means for electrically coupling the storage means to the heart. Determining means determine right atrial pressure or central venous pressure and right ventricular pressure. Means responsive to an output from the determining means provide a signal whenever a relationship between right atrial pressure or central venous pressure and right ventricular pressure reaches at least a predetermined value. Means responsive to the signal charge and enable discharge of the electrical energy stored by the storage means across the electrode means upon the relationship reaching at least the predetermined value.

From a slightly different viewpoint, the invention can be viewed as being in a system for treating a malfunctioning heart of the type which includes storage means for storing electrical energy and electrode means for electrically coupling the storage means to the heart. Determining means determine mean right atrial pressure or mean central venous pressure and right ventricular systolic pressure. Means respond to an output from the determining means and provide a signal whenever a relationship between mean right atrial pressure and right ventricular systolic pressure reaches at least a predetermined value. Means responsive to the signal charge and enable discharge of the electrical energy stored by the storage means across the electrode means upon the relationship reaching at least the predetermined value.

The invention can be seen broadly as a system for treating a malfunctioning heart of the type which includes storage means for storing electrical energy and electrode means for electrically coupling the storage means to the heart. Determining means for determining a first hemodynamic parameter and a second hemodynamic parameter in a circulatory system enable discharge of the electrical energy stored by the storage means across the electrode means upon the determining means indicating that a relationship between the first hemodynamic parameter and the second hemodynamic parameter has reached at least a predetermined value.

In its method aspect, the invention is a method of treating a malfunctioning heart which includes monitoring right atrial pressure or central venous pressure, monitoring right ventricular systolic pressure, and determining if a relationship (difference or ratio, for example) between right atrial pressure or central venous pressure and right ventricular pressure reaches at least predetermined value. The method provides for delivering cardioverting/defibrillating electrical energy to the heart upon determining that the relationship (difference or ratio, for example) between right atrial pressure or central venous pressure and right ventricular pressure has reached at least the predetermined value.

From a different viewpoint, the invention can be seen as a method of treating a malfunctioning heart comprising monitoring mean right atrial pressure or mean central venous pressure, monitoring right ventricular systolic pressure and determining if a relationship (difference or ratio) between mean right atrial pressure and right ventricular systolic pressure reaches at least predetermined value. The method involves also delivering cardioverting/defibrillating electrical energy to the heart upon determining that the relationship (difference or ratio) between mean right atrial pressure and right ventricular pressure has reached at least the predetermined value.

The invention can be broadly as a method of treating a malfunctioning heart which includes monitoring at least two hemodynamic parameters in a circulatory system and determining if a relationship between the first hemodynamic parameter and the second hemodynamic parameter has reached at least a predetermined value. The step of delivering cardioverting/defibrillating electrical energy to the heart is undertaken upon determining that the two hemodynamic parameters have reached at least the predetermined relationship to one another.

Current automatic implantable cardioverter-defibrillators detect tachyarrhythmias primarily by rate-only algorithms and cannot adequately distinguish hemodynamically stable from unstable tachyarrhythmias. Therefore, the responses of RA (mean) and RV pressure (mean, systolic, diastolic, and pulse) to 64 induced and paced tachyarrhythmias were studied in 10 patients (LV ejection fraction = $32 \pm 6\%$), to develop algorithms capable of differentiating hemodynamically stable from unstable rhythms. Tachyarrhythmias were defined as hemodynamically unstable if mean arterial pressure decreased by $\leq 25$ mmHg over 15 seconds. A combined heart rate, mean RA pressure, RV systolic pressure detection algorithm [Rate $-\Delta$MRAP $-\Delta$RVSP] was developed, such that if heart rate was $\leq 150$ b.p.m. and mean RA pressure increased by $\leq 6$ mmHg over 15 sec., a hemodynamically unstable rhythm was identified. This algorithm was then tested in an additional 20 patients (LV ejection fraction = $34 \pm 4\%$) and compared to the current rate-only algorithm (rate $\leq 150$ b.p.m.), 143 induced and paced tachyarrhythmias, and the sensitivity and specificity of detection of hemodynamically unstable tachyarrhythmias determined. The results were:

|  | Rate-only | Rate- $\Delta$MRAP-$\Delta$RVSP |
| --- | --- | --- |
| Sensitivity | 100% | 100% |
| Specificity | 68% | 100%. |

In addition, the rate-$\Delta$MRAP-$\Delta$ARVSP algorithm was capable of excluding perturbations from cough and Valsalva maneuver.

During the study, measurements of MRAP, RVSP, RVDP, RVPP MRVP and MAP were obtained and the results recorded as indicated in Table I below. As summarized below in Table I, cycle length: baseline was $701 \pm 30$ ms, VT/VF = $247 \pm 11$ ms, and after termination = $688 \pm 30$ ms. During VT/VF changes in MRAP, RVSP, RVPP, and MAP from baseline were significant at each measurement, and post VT/VF these pressures returned towards baseline and were significantly different from those after 30 seconds of VT/VF.

TABLE I

|  | Times(s) | MRAP | RVSP | RVDP | RVPP | MRVP | MAPmmHg |
| --- | --- | --- | --- | --- | --- | --- | --- |
| baseline | 0 | 7 + 1 | 39 + 2 | 7 + 1 | 32 + 3 | 15 + 1 | 80 + 4 |
| VT/VF | 5 | 11 ± 1 | 23 ± 2 | 9 ± 1 | 14 ± 2 | 13 ± 1 | 43 ± 3 |
|  | 15 | 14 ± 1 | 24 ± 1 | 11 ± 1 | 13 ± 2 | 15 ± 1 | 34 ± 3 |
|  | 30 | 18 + 1 | 27 + 2 | 14 + 2 | 13 + 3 | 19 + 1 | 37 + 4 |
| Post VT/VF | 30 | 11 + 1 | 50 + 3 | 11 + 1 | 39 + 3 | 20 + 2 | 86 + 5 |

Among other hemodynamic pressure parameters (not shown in Table I) suitable for use in practicing the present invention is central venous pressure (CVP) which is expected to vary in the same manner as RVP, as well as mean central venous pressure (MCVP) which is expected to vary in the same manner as MRVP. The invention can be practiced using hemodynamic parameters other than pressure parameters. For example, mixed venous $O_2$ saturation, pH, body temperature, blood temperature, heart temperature, cardiac output, cardiac impedance, ejection fraction, lactic acid level among others.

The novel features that are considered characteristic of the invention in its method and system aspects are set forth with particularity in the appended claims. The invention itself, however, both as to its organization and its method of operation, together with other objects and advantages thereof is to be understood from the following description of illustrative embodiments, when read in conjunction with the accompanying drawings, wherein like reference numerals refer to like components.

DETAILED DESCRIPTION OF THE PREFERRED EMBODIMENTS

Figure 1:
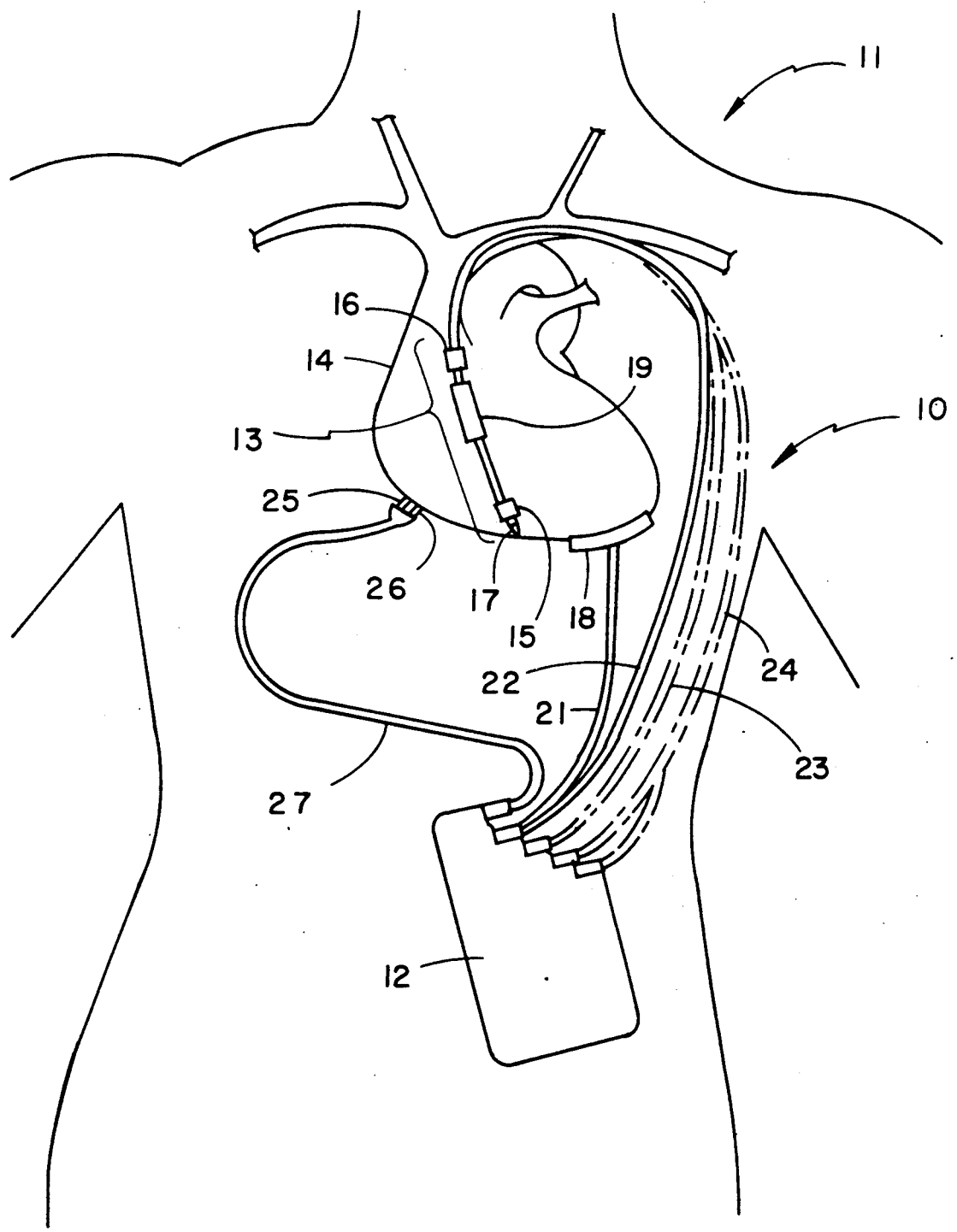
FIG. 1 is a diagrammatic, generalized illustration of an exemplary, implanted hemodynamically responsive system responsive to right-heart chamber pressure changes for treating a malfunctioning heart in accordance with the present invention, in particular to changes in mean right atrial (or ventricular) pressure and right ventricular systolic pressure.

As shown in FIG. 1, an exemplary embodiment of an automatic implantable cardioverter-defibrillator and antitachycardia system is designated generally by the numeral 10 and illustrated diagrammatically as being implanted within a human subject 11. The cardioverter-defibrillator system 10 includes an implanted housing 12 within which major circuit components of the system are housed. A catheter 13 is shown within the right side of a heart 14. The catheter 13 carries a first pressure sensor 15 positioned within the right ventricle and a second pressure sensor 16 positioned within the right atrium, in accordance with a preferred embodiment of the present invention. The second pressure sensor 16 could, were one to wish to sense central venous pressure (CVP), be positioned in the vena cava. It is believed that CVP varies in a manner similar to RAP and that MCVP varies in much the same fashion as MRAP. A heart rate sensor 17 is carried on the end of the catheter 13. A patch electrode 18 is positioned on the outside of the heart 14 at the apex thereof. The catheter 13 carries on its outer surface an electrode 19 which cooperates with the patch electrode 18 to deliver cardioverting/defibrillating energy to the heart 14. The pair of electrodes 18, 19 are provided for the purpose of delivering D.C. cardioverting-defibrillating energy from within the housing 12 to the heart 14 under control of circuitry within the housing, a pair of insulated leads 21 and 22 respectively being provided for this purpose. The heart rate sensing sensor 17 may be provided with one or more electrodes within the heart 14, these electrode(s) being positioned in tissue and being conductively coupled to circuitry within the housing 12 via an insulated cable 23. Further leads extend from the pressure responsive sensors 15 and 16 to circuitry within the housing 12 via an insulated cable 24. It is to be understood that were it desired to use MAP as a pressure parameter, in place of RVSP for example, an arm cuff setup shown in FIG. 2 and as illustrated in FIG. 26 of applicant's copending above-mentioned application Ser. No. 385,544, now U.S. Pat. No. 4,984,572 could be provided.

Pacemaking circuitry within the housing 12 may be provided to produce antitachycardia pacemaking signals, to a pair of pacing electrodes 25 and 26, illustrated as being fixed in tissue on the outside of the heart in the vicinity of the right ventricle. The pacing electrodes 25 and 26 are connected by respective conductive leads within a cable 27 which communicates with circuitry within the housing 12.

It is to be understood that the pacing lead, illustrated as the cable 27, could be arranged to be carried by the catheter 13 (or a separate one) so that the electrodes 25 and 26 (or a single pacing electrode) would contact tissue within the right side of the heart 14. It is contemplated that the present invention could be associated with conventional dual or single chamber pacing technology, depending on needs of the particular patients. Were dual chamber pacing to be desired, additional pacing electrodes would be provided. The pacing electrodes 25 and 26 could be positioned on the outside of the heart in the vicinity of the right atrium or contact tissue within the right atrium.

The heart rate wave (R-wave) sensor 17, is shown as being positioned near the apex of the heart 14 within the right ventricle, for purposes of illustration. It could be positioned in or on the heart 14 or, for that matter, on the exterior of a patient, as in conventional in ECG systems.

Figure 2:
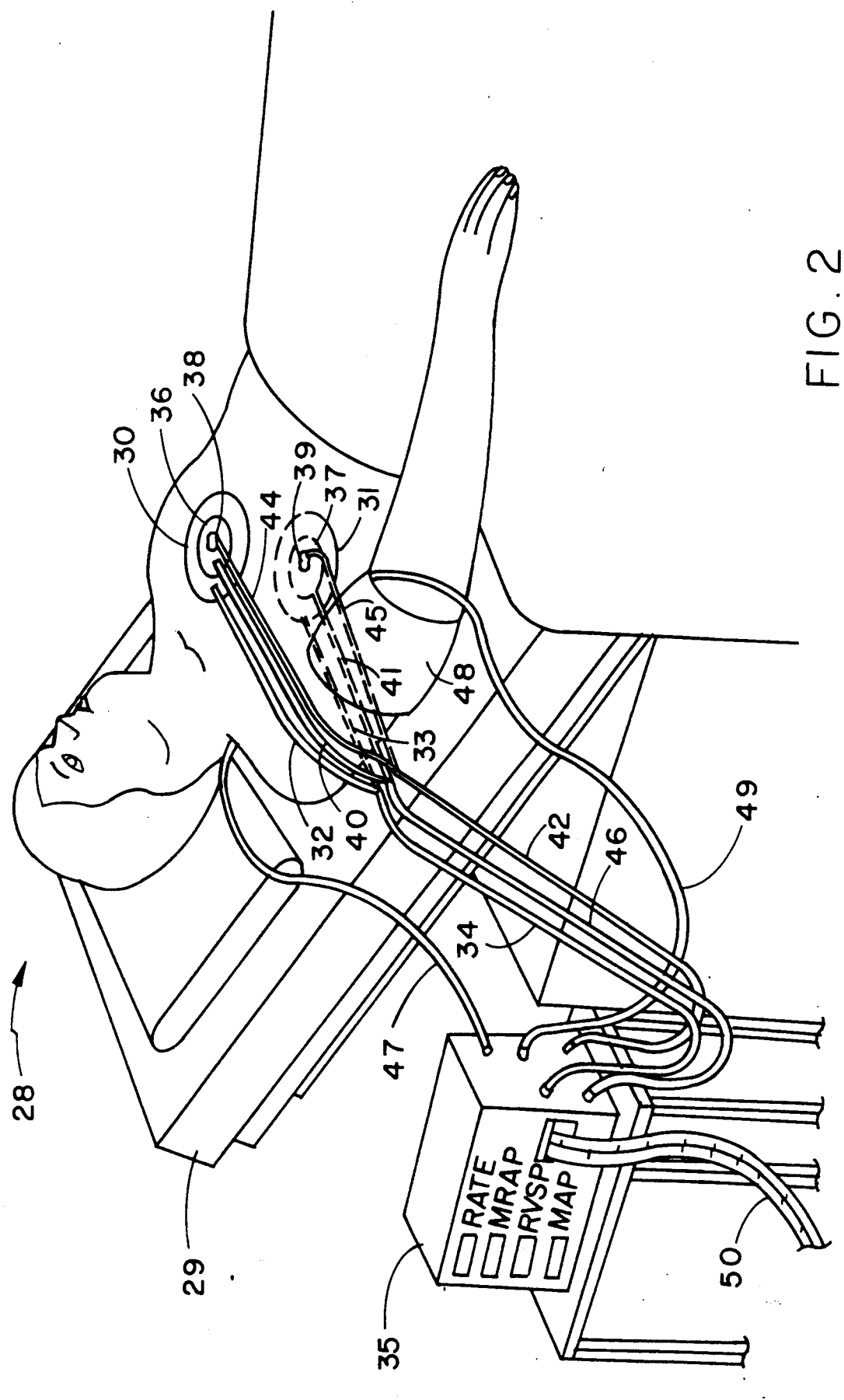
FIG. 2 is a partially diagramic illustration of an exemplary, external hemodynamically responsive system responsive to right-heart chamber pressure changes for treating a malfunctioning heart in accordance with the present invention.

In FIG. 2 a portion of a noninvasive system for sensing heart rate and pressure of the type which may be used in an intensive care unit (ICU), a recovery room, coronary care unit (CCU), and/or in a routine care patient facility is illustrated, as broadly incorporating the present invention. The system of FIG. 2 can be considered a system which can be substituted for the more invasive systems shown in FIG. 1. A patient 28 is shown in a reclined posture on a bed 29. A pair of pulse-delivering electrodes or patches 30 and 31 (substitutes for electrodes 18, 19; FIG. 1) are positioned respectively on the anterior and posterior chest of the patient 28 for the purpose of coupling cardioverting/defibrillation energy pulses to the patient, respective insulated leads 32 and 33 (substitutes for leads 21, 22; FIG. 1) being provided. A cable 34 is provided to conduct the cardioverting/defibrillating pulses to the patches 30 and 31, from pulse-generating circuitry within a housing 35 (substitute housing 12; FIG. 1). The leads 32 and 33 and patches 30 and 31 are to be used in place of the cardioverting/defibrillating electrodes 18 and 19 (FIG. 1), were the system of the present invention to be used in a noninvasive stand-alone or portable or patient-carried configuration, instead of in an implantable configuration as illustrated in FIG. 1. Positioned radially within the respective electrodes 30 and 31 and insulated therefrom, are respective pacing electrodes 36 and 37 (substitutes for electrodes 25, 26; FIG. 1). A pair of respective ECG rate (R-wave) sensing electrodes 38 and 39 (substitutes for rate sensor 17; FIG. 1) are provided centrally within and insulated from the pacing electrodes 36 and 37, respectively. The pair of ECG electrodes 38, 39 are connected respectively via respective insulated leads 44, 45 and a cable 42 to circuitry within the housing 35. The pair of pacing electrodes 36, 37 are connected respectively via respective insulated leads 44, 45 and a cable 46 to the circuitry within the housing 35.

A catheter (not visible in FIG. 2) is positioned within the right side of the heart of the patient 28. A pair of pressure transducers (sensors), which may be of the bending type or the compression type, like the pressure sensors 15 and 16 of FIG. 1, are carried by the catheter. Output leads from the pair of pressure sensors are coupled to the circuitry within the housing 35 via a cable 47.

If one wishes to measure or monitor arterial pressure and use mean arterial pressure as one of the sensed pressure parameters, a conventional automatically acting inflated cuff 48 may be provided and coupled, via a conduit 49 to pressure responsive circuitry within the housing 35. The circuitry within the housing may, if desired, be used to visually display heart rate, MRAP, RVSP and MAP, as illustrated; of course, other pressure parameters, such as CVP, MCVP, RVDP, RVPP and/or MRVP could be displayed as well, depending on which of the pressure parameters are to be used. An ECG tracing may be recorded on a strip 50.

Figure 3A:
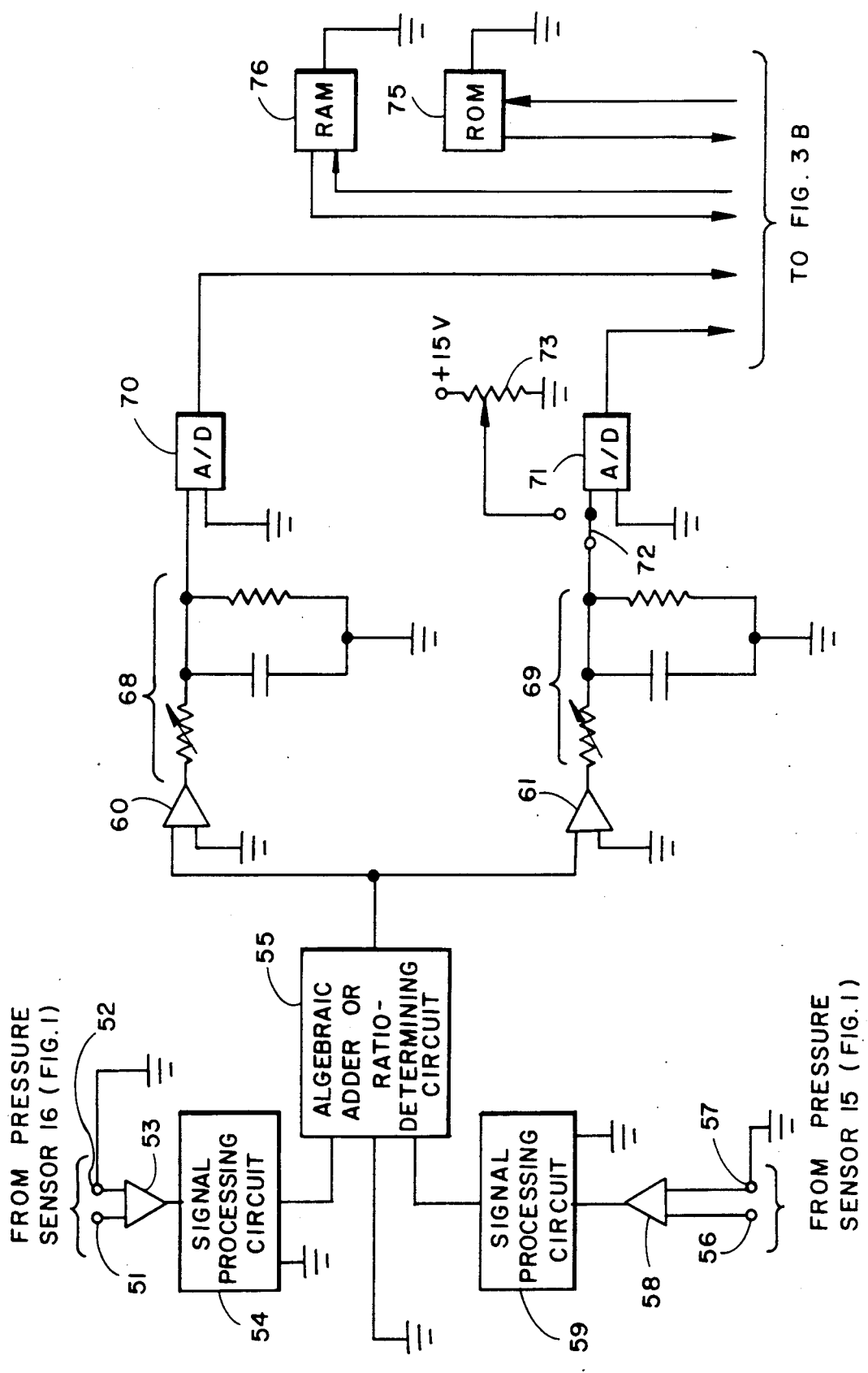
FIGS. 3A and 3B are a partially block, schematic diagram of a hemodynamically responsive system for treating a malfunctioning heart which is responsive to right-heart chamber pressure changes, in particular to changes in mean right atrial pressure and right ventricular systolic pressure or mean right ventricular pressure and right ventricular systolic pressure.
Figure 3B:
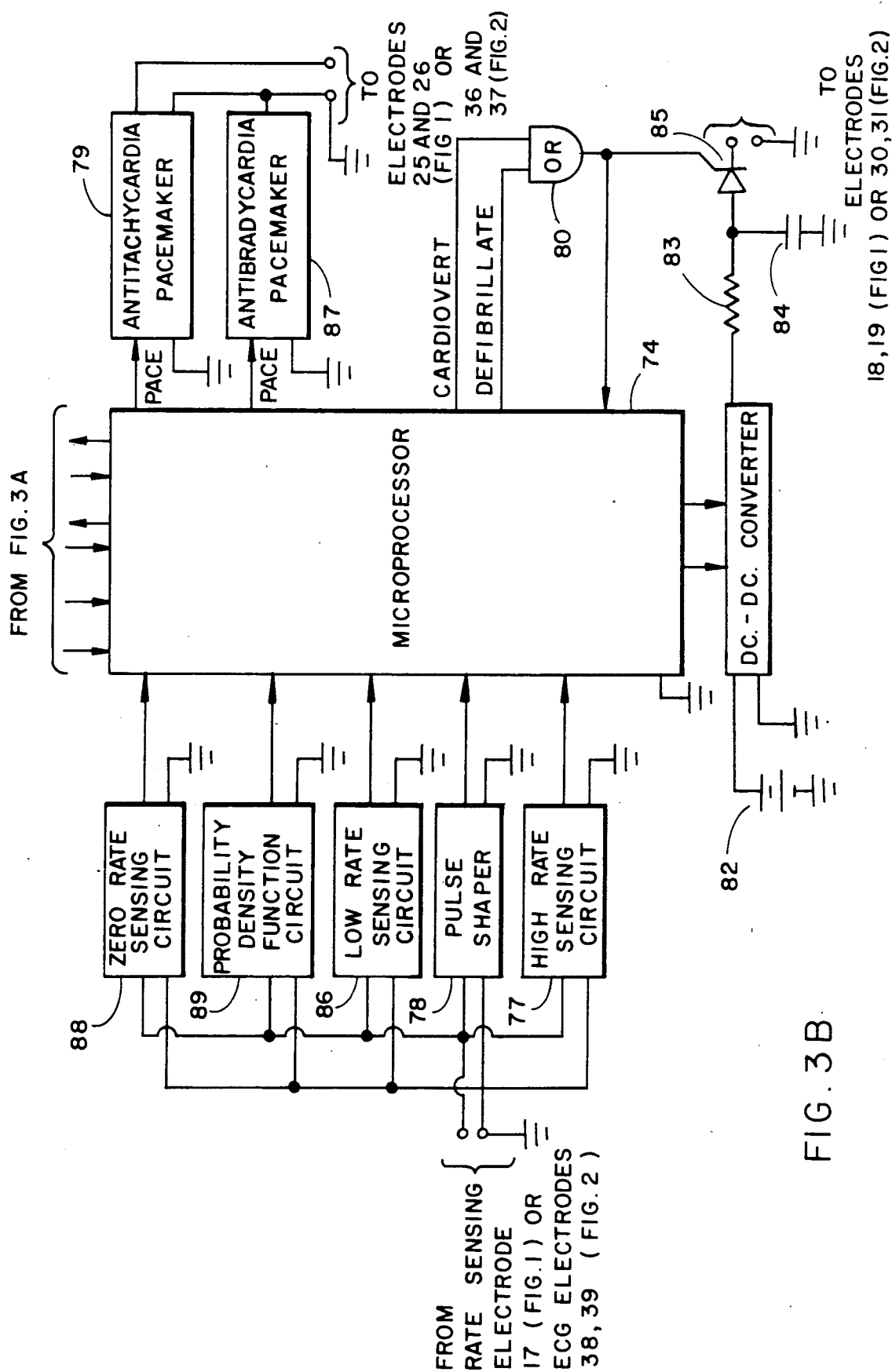

Turning to FIGS. 3A and 3B, an exemplary embodiment of circuit components of a system for treating a malfunctioning heart, which may be positioned within the housing 12 (FIG. 1) or in the housing 35 (FIG. 2) or used in a portable system which may be carried on the body of a patient or used in fixed installations, such as in ICU's, CCU's, hospital rooms and the like. The system includes a pair of input terminals 51, 52 which receive the variable D.C. voltage output signal representing pressure within the right atrium from the pressure sensor 16 (FIG. 1), the terminal 52 being connected to a point of circuit reference potential (ground). The terminals 51, 52 are connected to an amplifier 53, which amplifies the pressure representing D.C. input signal and feeds the same to a signal processing circuit 54 which operates to develop, for example, a signal representing the MRAP. A signal representing MRAP is fed from the signal processing circuit 54 to one input of a ratio-determining circuit or algebraic adder 55, which may be, were the difference between two inputs to be determined, an operational amplifier.

Similarly, a pair of input terminals 56 and 57 are provided and receive the variable D.C. voltage output signal from the sensor 15 (FIG. 1) representing pressure or within the right ventricle. The terminal 57 is connected to system ground. The terminals 56, 57 are coupled to the input terminals of an amplifier 58 which has its output, in turn, coupled to a signal processing circuit 59. The signal processing circuit 59, which may be constructed like the circuit illustrated in FIG. 21 in applicant's copending application Ser. No. 385,544, now U.S. Pat. No. 4,984,752 filed July 27, 1989, responds to its input and provides, as its output, a signal representing right ventricle systolic pressure (RVSP) within the right ventricle. Were one to desire to use, as one of the pressure parameters, right ventricle diastolic pressure (RVDP), right ventricle end diastolic pressure (RVEDP) or right ventricle pulse pressure (RVPP) the signal processing circuit 59 could be constructed respectively like the circuits illustrated respectively in FIGS. 22, 23 and 24A, 24B of applicant's copending application Ser. No. 385,544, now U.S. Pat. No. 4,984,572. The output from the signal processing circuit 59 is fed to a second input of the ratio-determining circuit or algebraic adder 55. The algebraic adder 55 produces an output signal which represents the current difference between the mean right atrial pressure (MRAP) and the right ventricle systolic pressure (RVSP). Were this circuit to be a ratio-determining circuit, it would produce an output representative of the ratio between MRAP and RVSP. The output signal from the circuit 55 is fed to two respective buffer amplifiers 60 and 61. It is to be understood that while MRAP and RVSP have been used as exemplary hemodynamic parameters, other hemodynamic parameters are suitable for practicing the present invention, including the pressure parameters set out above in Table I. It is believed that among other hemodynamic parameters which could be selected, in place of one or both of the pressure parameters, include mixed venous $O_2$ saturation, pH, body temperature, blood temperature, cardiac temperature, cardiac output, cardiac impedance, lactic acid level, an ion (potassium, for example) level and the like. Any hemodynamic parameter which can be determined from output from chronic sensors and varies in a predicatable fashion during or upon the onset of hemodynamic compromise or as a precursive indicator of compromise may be suitably be used in practicing the present invention.

The respective outputs from the buffer amplifiers 60 and 61 are fed to a pair of RC circuits 68 and 69, respectively, which develop respectively short term (current) and long term (baseline) signals reflecting the difference (or ratio ) between MRAP and RVSP, in the example given, which are converted into digital signals by respective analog-to-digital (A/D) converters 70 and 71. Were one to desire to provide a fixed baseline signal, instead of the varying baseline signal from the RC circuit 69, a single-pole, double-throw switch 72 would be set to receive a fixed, albeit adjustable, D.C. voltage from a potentiometer 73.

Outputs from each of the A/D converters 70 and 71 are connected to respective data input terminals of a microprocessor 74. The circuit of FIGS. 3A and 3B can be used in practicing the present invention using either the two site hemodynamic parameter criteria alone or both rate and the hemodynamic parameter criteria. The circuit of FIGS. 3A and 3B can be used to carry out the methods, illustrated as algorithms in the flowcharts of FIGS. 4 and 5. It is to be understood that the first step (looking at heart rate) need not be used, but is preferred.

The microprocessor-based circuitry of FIGS. 3A and 3B could be programmed to carry out other routines. For example, were a rate criterion to be satisfied, the circuit could be arranged (1) simply to monitor selected hemodynamic parameters, (2) to effect antitachycardia pacing and/or to cardiovert. As further examples, were both rate and the selected hemodynamic criteria to be satisfied, the circuit of FIGS. 3A and 3B could be programmed (1) to effect antitachycardia pacing and/or (2) to cardiovert/defibrillate. Moreover, the selected interventions could be programmed so that when one is tried and fails, another is tried and so on. For example, if a tachycardia were detected regardless of whether or not hemodynamic compromise is present an antitachycardia pacemaker would attempt early to revert the arrhythm to normal and if this fails cardioversion/defibrillation would then attempt the same.

The A/D converters 70 and 71, in operation, convert the respective analogue pressure-related signals into corresponding digital signals for processing by the microprocessor 74, the microprocessor having associated therewith a ROM 75, which supplies programmed instructions to the microprocessor, and a RAM 76, which stores and supplies digital signal representations of pressure-related signals, as well as other signals, from and to the microprocessor.

Another input of the microprocessor 74 is supplied with high (ONE) and low (ZERO) signals from a high rate sensing circuit 77, which produces a ONE signal whenever the heart rate, as sensed by the electrode 17 (FIG. 1) or by the electrodes 38 and 39 (FIG. 2), exceeds a predetermined rate, for example a rate of 150 b.p.m. The actual rate selected would, of course, depend on the individual patient and a professional opinion as to his or her condition. A pulse shaper 78, which also receives an input from the rate sensing electrode(s) is provided to supply narrow D.C. pulses to the microprocessor 74; if present, these pulses would be used as synchronizing pulses for cardioversion.

An antitachycardia pacemaker 79 is connected to an output terminal of the microprocessor 74 to receive therefrom a pace enable signal to, in effect, enable or turn on the pacemaker 79 under the command of the microprocessor 74. Two other output terminals from the microprocessor 74 provide respective cardiovert and defibrillate command signals to an OR circuit 80, which cooperates with a D.C.-to-D.C. converter 81, a battery 82, a charging resistor 83, storage capacitor 84 and a SCR 85 in the same manner as corresponding circuit components shown and described in the above-mentioned copending application Ser. No. 385,544, now U.S. Pat. No. 4,984,752 of applicant. The output of the OR gate 80 is also supplied to an input terminal of the microprocessor 74, supplying signals to a counting means within the microprocessor 74.

If desired for example, a low rate sensing circuit 86 could be provided, its input being coupled to the rate sensing electrode(s). The low rate sensing circuit 86 supplies a high (ONE) signal to an input terminal whenever the beating rate, as sensed, falls below a given rate, for example 45 b.p.m., an indication of bradycardia. Under these conditions (provided the rate were not zero), the microprocessor 74 would provide a command enable signal to an antibradycardia pacemaker 87. When enabled, the pacemaker 87 would supply bradycardia-correcting pacing signals to a patient's heart via the pacing electrodes 25 and 26 (FIGS. 1) or the pacing electrodes 36 and 37 (FIG. 2).

If desired, a zero rate sensing circuit 88, responsive to output from the rate sensing electrode(s) can be provided. This zero rate sensing circuit 88 produces a high (ONE) output signal whenever the beating rate is zero, indicating the heart has stopped beating (sometimes referred to as going "flat line"). This may represent either asystole or fine ventricular fibrillation. Under this condition, the microprocessor 74 is programmed to first effect a charging and discharging of the storage capacitor 84, supplying a ONE signal via its command defibrillate output connection to the OR gate 80 and then to effect antibrachycardia pacemaking after a given number of capacitor(s) discharges (say 4) if no hemodynamic improvement is noted. The order of defibrillation and pacemaking may be programmed in a reverse manner as desired.

The circuit of FIGS. 3A and 3B includes, if desired, a narrow window probability density function circuit 89, which has its input coupled to the sensing electrode(s). The probability density function circuit may be of the type disclosed in U.S. Pat. Nos. 4,184,493, 4,202,340 and 4,475,551 of Langer et al. and which produce a high (ONE) output signal whenever fine ventricular fibrillation is present. This ONE output is supplied to an input of the microprocessor 74 which, in accordance with its program stored in the ROM 75, effects the charging and discharging of the storage capacitor 84, supplying via its command defibrillate output a ONE signal to the OR gate 80 to initiate discharge.

Figure 4:
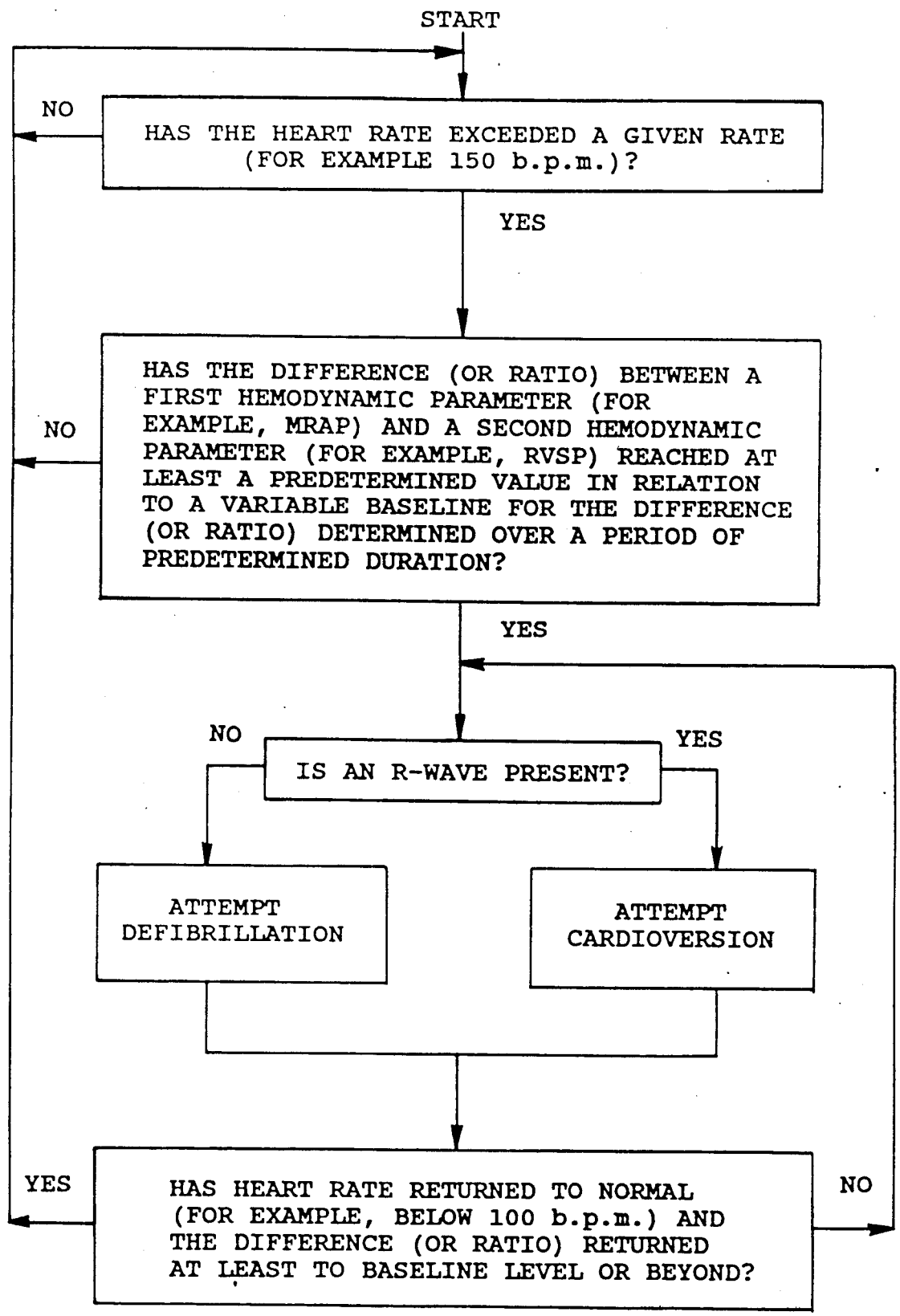
FIGS. 4 and 5 constitute respective exemplary flowcharts of a series of actions or steps which may be carried out by the system illustrated in FIGS. 3A and 3B, and effect achievement of respective method embodiments.
Figure 5:
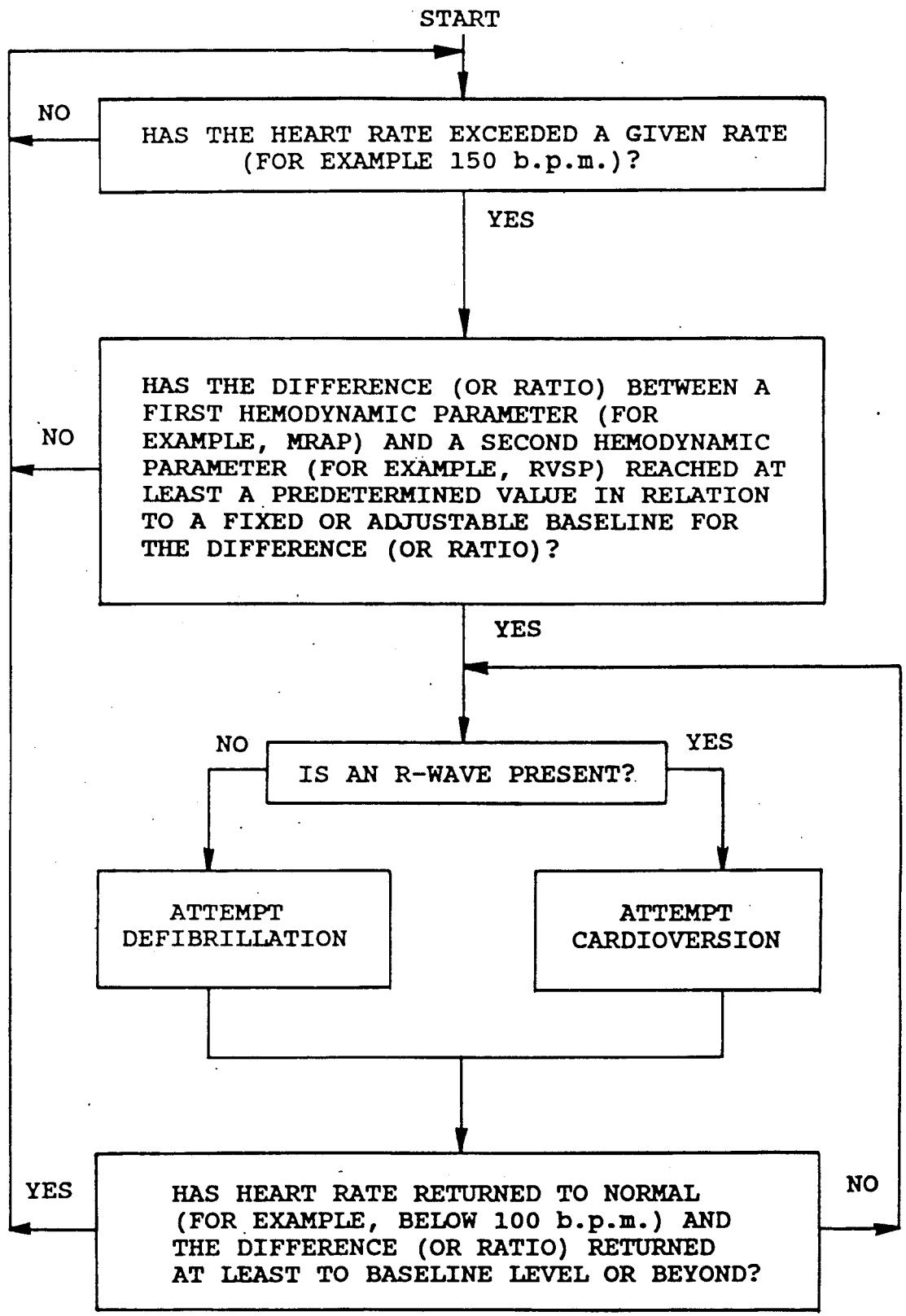

The respective exemplary flowcharts shown in FIGS. 4 and 5 set out a series of actions or steps which may be carried out by the system illustrated in FIGS. 3A and 3B to effect achievement of respective method embodiments. As illustrated, the flowcharts are concerned with two hemodynamic parameters (MRAP and RVSP are set out by way of example). It is to be understood that other pressure parameters (including those set out in TABLE I, as well as CVP or MCVP) and/or a different site or sites at which the pressure sensor(s) is (are) placed are within the scope of the present invention. For example, pulse pressures at other points in a circulatory system, such as right atrial pulse pressure (RAPP), could be used. The routines set out in FIGS. 4 and 5 are general in nature. The routines could be incorporated into more detailed routines. In some cases the heartbeat rate criterion need not be used as a screening step.

The foregoing description concerns systems and methods in which two or more distinct hemodynamic parameters, in particular changes therein, are used to determine if cardioversion/defibrillation is to be attempted. It is within the contemplation of applicant that the relationship between at least two pressure parameters, for example, the difference or ratio therebetween could be used as the basis for determining if cardioversion/defibrillation is to be attempted. In some cases, were the difference in two pressure parameters to be the selected criterion, the two sensors (transducers) may be connected in electrical series and oppositely poled.

It is to be understood that the foregoing detailed description and accompanying illustrations have been set out by way of example, not by way of limitation. Numerous other embodiments and variants are possible, without departing from the spirit and scope of the invention, its scope being defined in the appended claims.

What is claimed is:

1. In a system for treating a malfunctioning heart of the type which includes storage means for storing electrical energy, electrode means for electrically coupling the storage means to the heart, determining means for determining either right atrial pressure and right ventricular pressure or central venous pressure and right ventricular pressure, means responsive to an output from the determining means for providing a signal whenever a relationship between either right atrial pressure and right ventricular pressure or central venous pressure and right ventricular pressure reaches at least a predetermined value indicative of hemodynamic compromise, and means responsive to the signal for charging and enabling discharge of the electrical energy stored by the storage means across the electrode means upon the relationship reaching at least the predetermined value.

2. The system according to claim 1, wherein said determining means comprises means for determining either mean right atrial pressure and right ventricular systolic pressure or mean central venous pressure and right ventricular systolic pressure, and wherein said means responsive comprises means responsive to output from the determining means for providing a signal whenever a relationship between either mean right atrial pressure and right ventricular systolic pressure or mean central venous pressure and right ventricular systolic pressure reaches at least the predetermined value.

3. The system according to claim 2, including means for establishing a fixed signal baseline representation of the predetermined value of the relationship between either mean right atrial pressure and right ventricular systolic pressure or mean central venous pressure and right ventricular systolic pressure.

4. The system according to claim 2, including means for establishing a variable signal baseline representation of the predetermined value of the relationship between either mean right atrial pressure and right ventricular systolic pressure or mean central venous pressure and right ventricular systolic pressure determined over a predetermined period of time.

5. The system according to claim 2, wherein said means responsive to output form the determining means comprises means responsive to output from the determining means for providing a signal whenever the difference between either mean right atrial pressure and right ventricular systolic pressure or mean central venous pressure and right ventricular systolic pressure reaches at least a predetermined value.

6. The system according to claim 2, wherein said means responsive to output from the determining means comprises means responsive to output from the determining means for providing a signal whenever the ratio between either mean right atrial pressure and right ventricular systolic pressure or mean central venous pressure and right ventricular systolic pressure reaches at least a given value.

7. The system according to claim 1, wherein the means responsive to the signal includes a microprocessor for developing a control signal to control the means for charging and enabling discharge of the electrical energy stored by the storage means.

8. The system according to claim 1, including electrical means for sensing heart rate and producing a distinctive control signal upon the heart rate exceeding a predetermined rate, and wherein the means responsive to the first-said signal enables discharge of the storage means upon contemporary presence of the first-said signal and the control signal.

9. The system according to claim 8, including antitachycardia pacemaking means, responsive solely to the distinctive control signal during periods when the first-said signal is absent, for delivering pacing signals to the heart whereby tachycardia may be overcome.

10. The system according to claim 8, including means responsive to output from said electrical means for sensing heart rate for developing a discharge-synchronizing signal synchronized to an R-wave, and wherein the means for discharging electrical energy across the electrode means and into the heart includes means for synchronizing the discharge with the discharge-synchronizing signal to effect cardioversion.

11. The system according to claim 10, wherein the means for discharging electrical energy across the electrode means and into the heart effects discharge on a nonsynchronized basis, in the absence of the synchronization signal, to effect defibrillation.

12. The system according to claim 1, including means for discharging electrical energy across said electrode means and into the heart effects discharge on a nonsynchronized basis to effect defibrillation.

13. The system according to claim 1, including means for establishing a fixed signal baseline representation of either the predetermined value of the relationship between right atrial pressure and right ventricular or central venous pressure and right ventricular pressure.

14. The system according to claim 1, including means for establishing a variable signal baseline representation of the predetermined value of the relationship between either right atrial pressure and right ventricular pressure or central venous pressure and right ventricular pressure determined over a predetermined period of time.

15. The system according to claim 1, wherein said means responsive to output from the determining means comprises means responsive to output from the determining means for providing a signal whenever the difference between either right atrial pressure and right ventricular pressure or central venous pressure and right ventricular pressure reaches at least a predetermined value.

16. The system according to claim 1, wherein said means responsive to output form the determining means comprises means responsive to output form the determining means for providing a signal whenever either the ratio between right atrial pressure and right ventricular pressure or central venous pressure and right ventricular pressure reaches at least a given value.

17. In a system for treating a malfunctioning heart of the type which includes storage means for storing electrical energy, electrode means for electrically coupling the storage means to the heart, determining means for determining a first hemodynamic parameter and a second hemodynamic parameter, means responsive to an output from the determining means for providing a signal whenever a relationship between the first and second hemodynamic parameters reaches at least a predetermined value indicative of hemodynamic compromise, and means responsive to the signal for charging and enabling discharge of the electrical energy stored by the storage means across the electrode means as at least one cardioverting pulse upon the relationship reaching at least the predetermined value.

18. The system according to claim 17, wherein the means responsive to the signal includes a microprocessor for developing a control signal to control the means for charging and enabling discharge of the electrical energy stored by the storage means.

19. The system according to claim 17, including electrical means for sensing heart rate and producing a distinctive control signal upon the heart rate exceeding a predetermined rate, and wherein the means responsive to the first-said signal enables discharge of the storage means upon contemporary presence of the first-said signal and the control signal.

20. The system according to claim 19, including antitachycardia pacemaking means, responsive solely to the distinctive control signal during periods when the first-said signal is absent, for delivering pacing signals to the heart whereby tachycardia may be overcome.

21. The system according to claim 19, including means responsive to output from said electrical means for sensing heart rate for developing a discharge-synchronizing signal synchronized to an R-wave, and wherein the means for discharging electrical energy across the electrode means and into the heart includes means for synchronizing the discharge with the discharge-synchronizing signal to effect cardioversion.

22. The system according to claim 21, wherein the means for discharging electrical energy across the electrode means and into the heart effects discharge on a nonsynchronized basis, in the absence of the synchronization signal, to effect defibrillation.

23. The system according to claim 17, including means for discharging electrical energy across said electrode means and into the heart effects discharge on a nonsynchronized basis to effect defibrillation.

24. The system according to claim 17, including means for establishing a fixed signal baseline representation of the predetermined value of the relationship between the first hemodynamic parameter and the second hemodynamic parameter.

25. The system according to claim 17, including means for establishing a variable signal baseline representation of the predetermined value of the relationship between the first hemodynamic parameter and the second hemodynamic parameter determined over a predetermined period of time.

26. The system according to claim 17, wherein said means responsive to output from the determining means comprises means responsive to output from the determining means for providing a signal whenever the difference between the first hemodynamic parameter and the second hemodynamic parameter reaches at least a predetermined value.

27. The system according to claim 17, wherein said means responsive to output from the determining means comprises means responsive to output from the determining means for providing a signal whenever the ratio between the first hemodynamic parameter and the second hemodynamic parameter reaches at least a given value.

28. A method of treating a malfunctioning heart comprising monitoring either right atrial pressure or central venous pressure, monitoring right ventricular pressure, determining if a relationship between either right atrial pressure and right ventricular pressure or central venous pressure and right ventricular pressure reaches at least predetermined value indicative of hemodynamic compromise, and delivering cardioverting/defibrillating electrical energy to the heart upon determining that the relationship between either right atrial pressure and right ventricular pressure or central venous pressure and right ventricular pressure has reached at least the predetermined value.

29. The method according to claim 28, wherein the steps of monitoring comprise monitoring mean right atrial pressure and right ventricular systolic pressure or mean central venous pressure and right ventricular systolic pressure, wherein the determining step comprises determining if a relationship between either mean right atrial pressure and right ventricular systolic pressure or mean central venous pressure and right ventricular systolic pressure reaches at least the predetermined value, and wherein the delivering step comprises delivering cardioverting/defibrillating electrical energy to the heart upon determining that the relationship between either mean right atrial pressure and right ventricular pressure or mean central venous pressure and right ventricular pressure has reached at least the predetermined value.

30. The method according to claim 29, including sensing heart rate, the step of delivering cardioverting-/defibrillating electrical energy being taken only upon the heart rate exceeding a given rate.

31. The method according to claim 29, including establishing a fixed baseline for the predetermined value.

32. The method according to claim 29, including establishing a variable baseline for the predetermined value based on a relationship between either mean right atrial pressure and right ventricular systolic pressure or mean central venous pressure and right ventricular systolic determined over a predetermined period of time.

33. The method according to claim 28, including sensing heart rate, the step of delivering cardioverting-/defibrillating electrical energy being taken only upon the heart rate exceeding a given rate.

34. The method according to claim 28, including establishing a fixed baseline for the predetermined value.

35. The method according to claim 28, including establishing a variable baseline for the predetermined value based on a relationship between either right atrial pressure and right ventricular pressure or central venous pressure and right ventricular pressure determined over a predetermined period of time.

36. A method of treating a malfunctioning heart comprising monitoring a first hemodynamic parameter, monitoring a second hemodynamic parameter, determining if a relationship between the first hemodynamic parameter and the second hemodynamic parameter reaches at least predetermined value, and delivering at least one pulse of cardioverting/defibrillating electrical energy to the heart upon determining that the relationship between the first hemodynamic parameter and the second hemodynamic parameter indicative of hemodynamic compromise has reached at least the predetermined value.

37. The method according to claim 36, including sensing heart rate, the step of delivering cardioverting-/defibrillating electrical energy being taken only upon the heart rate exceeding a given rate.

38. The method according to claim 36, including establishing a fixed baseline for the predetermined value.

39. The method according to claim 36, including establishing a variable baseline for the predetermined value based on a relationship between the first hemodynamic parameter and the second hemodynamic parameter determined over a predetermined period of time.

40. The method according to claim 36, wherein at least one of the hemodynamic parameters is a nonpressure parameter.

41. The method according to claim 36, wherein the at least one parameter is mixed venous $O_2$ saturation, pH, body temperature, blood temperature, cardiac output, cardiac impedance, lactic acid level or a blood ion level.

42. In a system for treating a malfunctioning heart of the type which includes storage means for storing electrical energy and electrode means for electrically coupling the storage means to the heart, an improvement comprising determining means for determining a first hemodynamic parameter and a second hemodynamic parameter in a circulatory system, and means for enabling discharge of the electrical energy stored by the storage means across the electrode means as at least one pulse of cardioverting/defibrillating energy upon output from the determining means indicating that a relationship between the first hemodynamic parameter and the second hemodynamic parameter has reached at least a predetermined value indicative of hemodynamic compromise.

43. A method of treating a malfunctioning heart comprising monitoring at least two hemodynamic parameters in a circulatory system, determining if a relationship between the first hemodynamic parameter and the second hemodynamic parameter reach at least a predetermined value indicative of hemodynamic compromise, and delivering cardioverting/defibrillating electrical energy to the heart upon determining that the relationship between the hemodynamic parameters has reached at least the predetermined value.

* * * * *

UNITED STATES PATENT AND TRADEMARK OFFICE
CERTIFICATE OF CORRECTION

PATENT NO. : 5,054,485
DATED : October 8, 1991
INVENTOR(S) : Cohen

It is certified that error appears in the above-identified patent and that said Letters Patent is hereby corrected as shown below:

In column 5, line 42, change "$\Delta$ARVSP" to -- $\Delta$ RVSP --.

In column 9, line 7, change "4,984,752" to -- 4,984,572 --.

In column 10, line 50, change "4,984,752" to -- 4,984,572 --.

Signed and Sealed this

Twenty-eighth Day of September, 1993

Attest:

BRUCE LEHMAN

*Attesting Officer*  *Commissioner of Patents and Trademarks*